US00PP18101P3

(12) United States Plant Patent

Graves et al.

(10) Patent No.: US PP18,101 P3

(45) Date of Patent: Oct. 2, 2007

(54) SEASIDE ALDER NAMED 'SEPTEMBER SUN'

(50) Latin Name: ***Alnus maritima* subsp. *oklahomensis***
Varietal Denomination: September Sun

(75) Inventors: William R. Graves, Ames, IA (US); James A. Schrader, Boone, IA (US)

(73) Assignee: Iowa State University Research Foundation, Ames, IA (US)

( * ) Notice: Subject to any disclaimer, the term of this patent is extended or adjusted under 35 U.S.C. 154(b) by 61 days.

(21) Appl. No.: 10/719,164

(22) Filed: Nov. 21, 2003

(65) Prior Publication Data

US 2005/0114959 P1 May 26, 2005

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

| | | | | | |
|---|---|---|---|---|---|
| PP14,821 | P2 | * | 5/2004 | Wood | Plt./226 |
| PP15,571 | P2 | * | 2/2005 | Robb | Plt./226 |
| 2005/0114959 | P1 | * | 5/2005 | Graves et al. | Plt./226 |

OTHER PUBLICATIONS http://www.hort.purdue.edu/newcrop/duke_energy/Alnus_maritima.html.*

Graves, William R. and James A. Schrader "'September Sun' Seaside alder: An autumn–blooming shrub native to North America" Hortscience 39(2): p. 438–439 Apr. 2004.*

Tebbitt, M.S. "International Registration of cultivar names for unassigned woody genera Jul. 2002–Jun. 2003" HortScience vol. 38(6): p. 1300. 2003.*

Anthony Huxley, ed. "*Alnus maritima*" The New Royal Horticultural Society Dictionary of Gardening vol. 1, The Stockton Press, New York, 1992, p. 118.*

Schrader, J.A., et al., "Infraspecific Systematics of *Alnus maritima* (Betulaceae) from Three Widely disjunct Provenances," Castanea 67(4):380–401. Dec. 2002.

Schrader, J.A., et al., "Phenology and depth of Cold Acclimation in the Three Subspecies of *Alnus maritima,*" J.Amer, soc. Hort. Sci. 128(3):330–336. 2003.

Schrader, J.A., et al., "Systematics of *Alnus maritima* (Seaside Alder) Resolved by ISSR Polymorphisms and Morphological Characters," J.Amer. Soc. Hort. Sci. 129(2),2004.

* cited by examiner

*Primary Examiner*—Wendy Haas
(74) *Attorney, Agent, or Firm*—Quarles & Brady LLP

(57) ABSTRACT

A new variety of *Alnus maritima* subsp. *oklahomensis* plant named 'September Sun' that is characterized by fast vertical growth of ≈89 cm (35 inches) per year over the first two years after establishment in the landscape and fast canopy volume growth of ≈4.8 m3 (170 cubic feet) during the second year after establishment. The strobili (infructescences) of 'September Sun' are small (17 mm long and 10.2 mm wide) and slender (length:width ratio=1.7) compared to the average for *oklahomensis*. In combination, these traits set 'September Sun' apart from all other existing varieties of *Alnus maritima* subsp. *oklahomensis* known to the inventors.

3 Drawing Sheets

STATEMENT REGARDING FEDERALLY SPONSORED RESEARCH OR DEVELOPMENT

Development of this technology was federally funded under the following USDA/CSREES grants: 98-CRHF-0-6019; 99-CRHF-0-6019; 00-CRHF-0-6019; 2001-31100-06019; 2002-31100-06019; 2003-31100-06019.

Botanical designation:

*Alnus maritima,* subspecies *oklahomensis.*

Variety denomination: 'September Sun.'

BACKGROUND

The present invention relates to the field of ornamental plants.

The present invention is a new and distinct variety of *Alnus maritima,* commonly known as "Seaside Alder," that is grown and utilized as an ornamental landscape tree or shrub. The new variety is known botanically as *Alnus*

*maritima* subsp. *oklahomensis* and will be referred to hereinafter by the variety name, 'September Sun.'

Plants of *Alnus maritime* are native to North America, and plants of subspecies *oklahomensis* specifically are native only to Oklahoma. The species is valued ornamentally for its dark green foliage, its bright-yellow, pendulous catkins that bloom in autumn, and its healthy appearance under conditions known to be stressful for other woody taxa. Subspecies *oklahomensis* is the most distinct of the three subspecies of *Alnus maritima* and represents the best of the species' ornamental and physiological traits. Efforts to develop superior cultivated varieties of subsp. *oklahomensis* began only recently in 1998.

Germplasm for 'September Sun' was obtained as seed from an open-pollinated parent growing naturally near Tishomingo, Okla. The inventors selected 'September Sun' as a single whole plant from a large seedling trial at Ames, Iowa in 2000. The inventors selected and confirmed 'September Sun' to be unique within subsp. *oklahomensis* for its faster growth, denser foliage, more symmetrical growth habit, and smaller, more slender infructescences shown in field trials with over 1000 plants. The vertical growth rate of 'September Sun' was shown to be approximately 73% greater than the mean for other genotypes of subsp. *oklahomensis,* and it volume growth rate greater than the mean. The strobili (cone-line infructescences) of 'September Sun' are 11% shorter and 18% smaller in diameter than the mean for other genotypes of subsp. *oklahomensis.*

The inventors carried out the first asexual propagation of 'September Sun' in 2000 at Ames, Iowa by rooting softwood cuttings of the original single plant. All of the resulting plants exhibited the typical characteristics of 'September Sun'. The inventors determined from successive generations of asexual propagation that the new variety 'September Sun' is stable and propagates true to type.

'September Sun' is registered with the International Cultivar Registration Authority, Brooklyn Botanical Garden (international authority for unassigned woody ornamentals), 1000 Washington Avenue, Brooklyn, N.Y. 11225-1099.

BRIEF SUMMARY

The following traits have been consistently observed, and represent the characteristisc of the new variety 'September Sun.' These traits in combination distinguish this variety from naturally occurring genotypes of subspecies *oklahomensis* and from other commercially available varieties known to the inventors. 'September Sun' has not been tested under all possible conditions, and phenotypic differences may be observed with variation in environmental, climatic and cultural conditions.

1. 'September Sun' is fast growing, with vertical growth of ≈89 cm (35 inches) per year over the first two years after establishment in the landscape (73% faster growth than the average genotype of subsp. *oklahomensis*). Canopy volume growth is extremely fast with an increase of ≈4.8 $m^3$ (170 cubic feet) during the second year after establishment (234% faster growth than the average genotype of subsp. *oklahomensis*).
2. The strobili (infructescences) of 'September Sun' are small and slender. They measure ≈17 mm long and 10.2 mm wide, with a length to width ratio of 1.7 (11% shorter and 18% smaller in diameter than the average).
3. 'September Sun' is densely foliated (relative to the subsp.); with a foliage density rating of 10 (1=least dense; 10 is most dense); whereas the average density rating for other genotypes of subsp. *oklahomensis* is 7.
4. 'September Sun' has a consistently symmetrical growth habit with a symmetry rating of 10 (1=least symmetry, 10=most symmetry) whereas the average symmetry rating for other genotypes of subsp. *oklahomensis* is 8.

SUMMARY OF THE INVENTION

The present invention is summarized in a new variety of ornamental plant of the species *Alnus maritima* subsp. *oklahomensis.* The new variety is named 'September Sun' and is characterized by rapid growth and fall foliage color.

BOTANICAL DESCRIPTION OF THE PLANT

Figure 1:
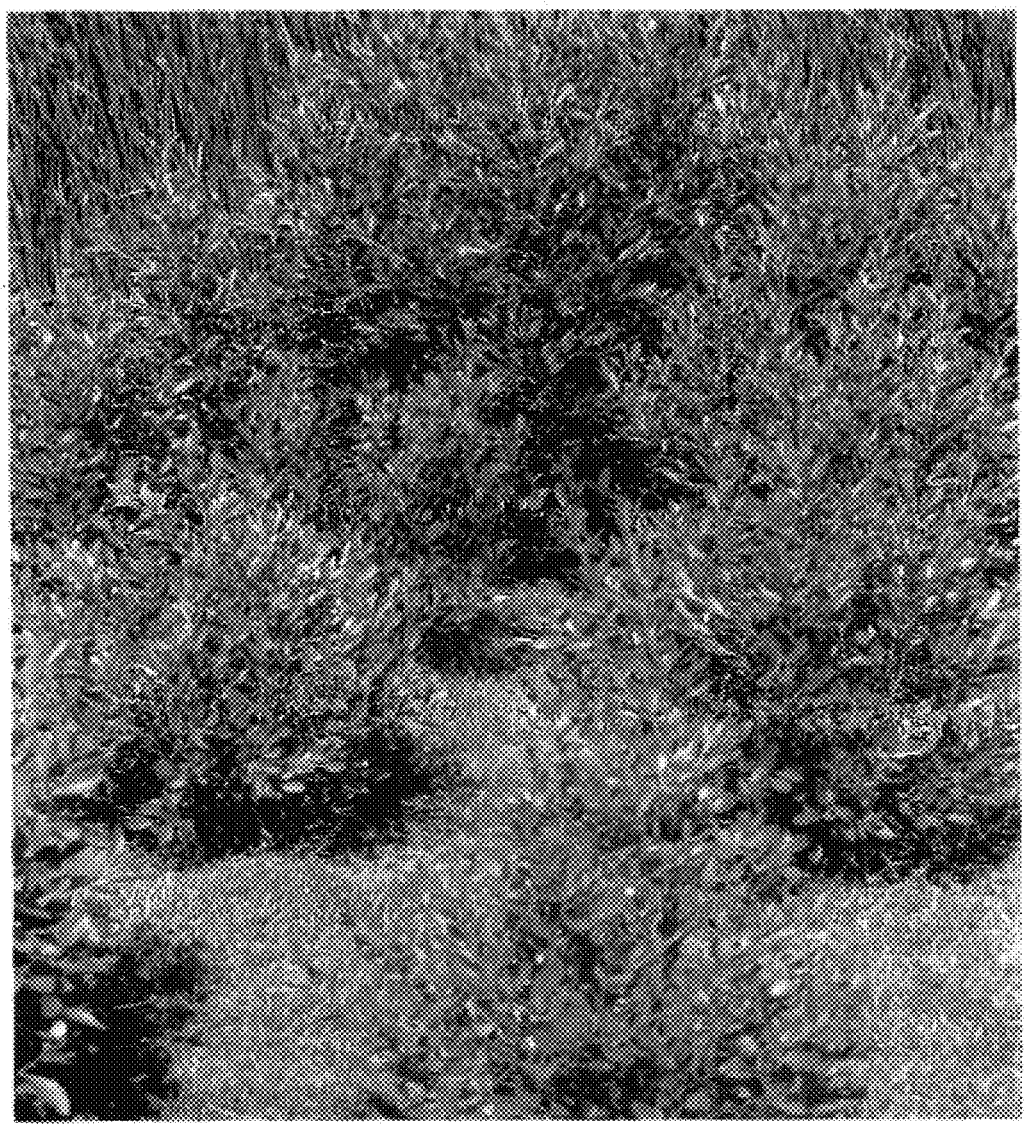
FIG. 1 is an illustration of the habit of the typical seaside alder 'September Sun' in an image showing several plants of the variety with similar habits.
Figure 2:
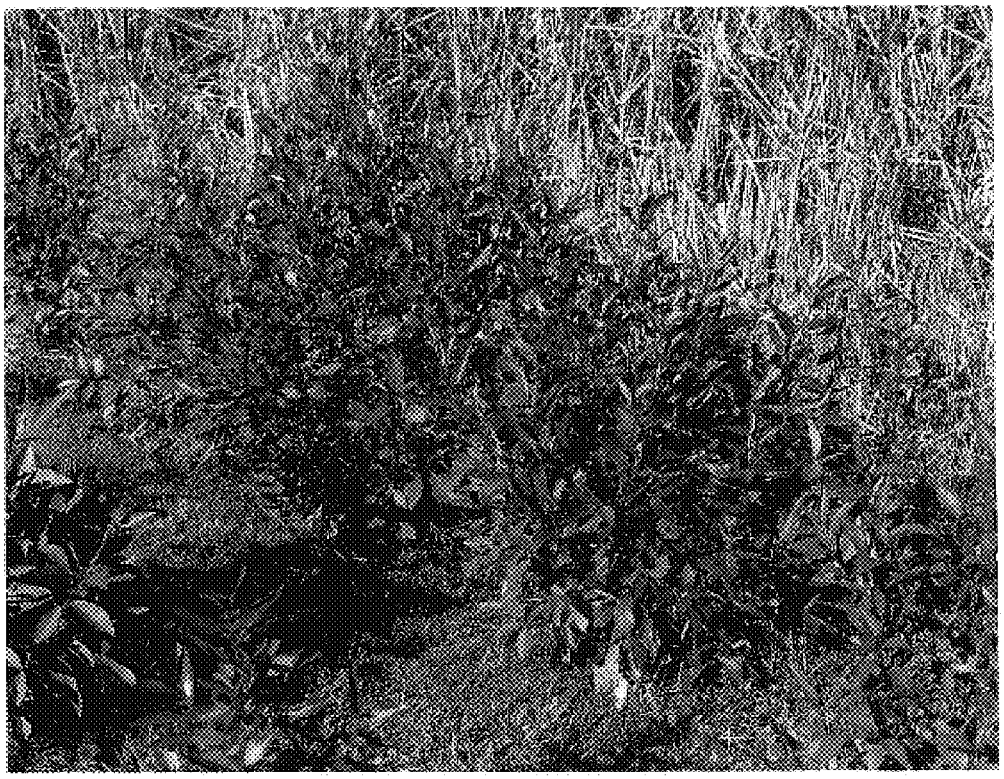
FIG. 2 is an illustration of the fall foliage of the seaside alder 'September Sun' in an image showing several plants of the variety with similar fall foliage.
Figure 3:
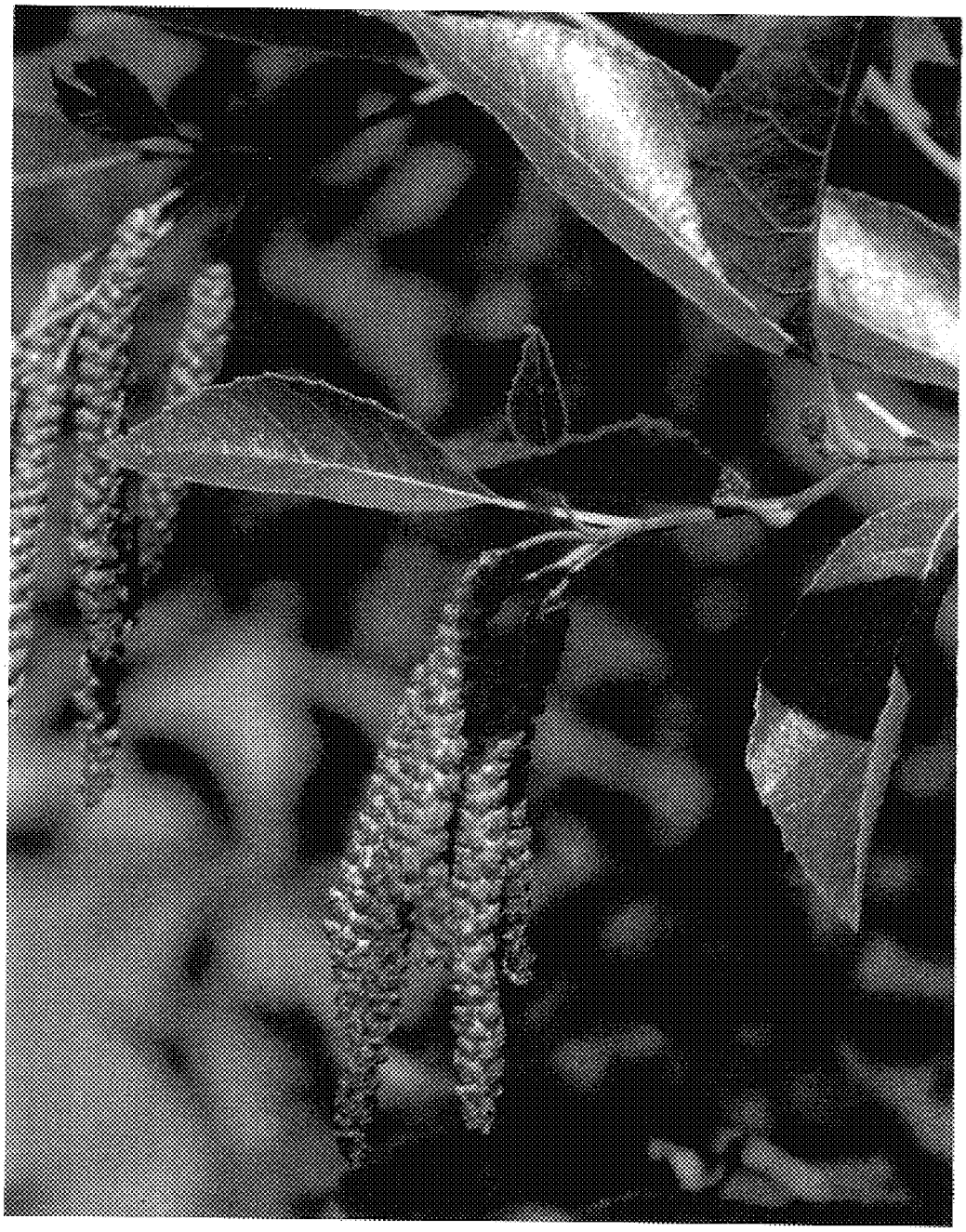
FIG. 3 is an enlarged view of the foliage and catkins of the seaside alder 'September Sun.'

The following is a description of the new variety, 'September Sun'. Data were collected from plants grown in outdoor conditions in field trials at Ames, Iowa, and plants were approximately three years old at the time of data collection.

Detailed descriptions and a key for the subspecies of *Alnus maritima* are provided in Schrader and Graves (2002).

Botanical classification: *Alnus martima* (Marsh.) Muhl. ex Nutt. subsp. *oklahomensis* Schrader & Graves 'September Sun'.

Commercial classification: Shrub or small tree for planting in the landscape.

Common names: Seaside Alder, Oklahoma Alder.

Use: Ornamental or windbreak plant for use in hedging or as a landscape specimen.

Parentage: Open-pollinated seed parent *Alnus maritima* subsp. *oklahomensis* growing on the bank of the Blue River near Tishomingo, Okla. (lat. 34°19'38"N., long. 96°35'25"W.).

Plant description:

*Bloom period.*—Early autumn.

*Plant habit.*—Upright large shrub with a broad-rounded crown.

*Height.*—2.4 m (7.9 ft.) after three years; 7 m (23 ft.) at full size if unpruned.

*Width.*—1.8 m (5.9 ft.) after three years; 6 m (20 ft.) at full size if unpruned.

*Hardiness.*—USDA Zones 4 through 9.

*Propagation.*—By softwood cuttings. Rooting is optimized with rooting compound.

*Time to develop roots.*—6 to 9 weeks under intermittent mist.

*Crop time.*—From 6 to 8 months are needed to produce a plant large enough for landscape installation. Plants flower during second season in the landscape.

*Pest and disease issues.*—None of note.

*Cultural requirements.*—'September Sun' is tolerant of partial shade and a wide range of soil types and conditions, but grows best in full sun and wet soils.

Stem:

*Shape.*—Cylindrical.

*Color.*—Young stems light green becoming brown. Bark is brown when new, then turning light gray and becoming darker gray with age.

*Surface.*—Bark smooth, becoming slightly rough with age, with lenticels near the base.

*Branching habit.*—Strong axillary branching. Single trunk first season, multiple trunks thereafter.

Foliage:

*Type.*—Deciduous.

*Shape.*—Blade ovate, elliptic or narrowly elliptic. Apex acute, sometimes acuminate.

*Size.*—Blade 7.5 cm to 9 cm long, 3 cm to 4 wide. Petiole 13 mm to 21 mm long, 0.75 mm to 1.5 mm in diameter.

*Margin.*—Serrate with single ascending teeth.

*Arrangement.*—Alternate.

Inflorescence:

*Staminate.*—1 to 6 catkins in racemose clusters at ends of current year's twigs. At anthesis, yellow and pendent, 2 cm to 8 cm long, 5 mm to 7 mm in diameter, on peduncles 4 mm to 18 mm long, 0.5 mm to 1 mm in diameter.

*Pistillate.*—Solitary in axils of the first to fourth leaves from apex, on twigs bearing staminate catkins. At anthesis, erect, ovate to elliptic, 3 mm to 4.5 mm long, 1.5 mm to 2.5 mm in diameter, on peduncles 5 mm to 7 mm long, 1 mm to 2 mm in diameter.

*Anthesis.*—Mid-August to mid-September.

Infructescence:

*Type.*—Cone-like strobili.

*Shape.*—Ovoid or ellipsoid; length to width ratio of 1.7.

*Size.*—≈17 mm long and 10.2 mm wide, on peduncles 5 mm to 10 mm long, 1 mm to 2 mm in diameter.

*Maturation.*—One year after pollination. Fruit drop December to March. Strobili persist on plants 1 to 2 years after fruit drop.

*Fruits.*—Light to dark brown, elliptic, 1 mm to 3 mm long, 1 to 2 mm wide, with wings narrow to absent and two persistent styles 0.4 mm to 0.8 mm long.

A herbarium specimen of 'September Sun' [May 18, 2003, *J. Schrader* 123 (ISC)] is on deposit at the Ada Hayden Herbarium (ISC), Iowa State University, Ames, Iowa 50011. A photograph and herbarium specimen of 'September Sun' have been deposited at the Brooklyn Botanical Garden (international registration authority for unassigned woody ornamentals), 1000 Washington Avenue, Brooklyn, N.Y. 11225-1099.

The cultivar 'September Sun' differs from other known genotypes of its species as it is the fastest growing, most densely foliated, and most symmetrically shaped individual plants that have been observed in field trials including over one thousand plants of the subspecies conducted to date. During a trial that was conducted over three growing seasons at a site in Ames, Iowa, 'September Sun' grew larger and developed a more symmetrically canopy shape than did other seedlings of *A. maritima* subsp. *oklahomensis* in that trial, including half-siblings of the original 'September Sun' plant. Shown below in Table 1 is an illustration of the trunk and size characteristics of four representative plants of this subspecies grown in this trial.

TABLE 1

| Genotype ($m^3$) | Trunk diam[z] (mm) | Canopy height[y] (cm) | Canopy volume[x] |
|---|---|---|---|
| 'September Sun' | 30.8 a[w] | 238.9 a | 6.17 a |
| 'Blue River #6' (unpatented) | 23.0 ab | 166.3 b | 2.35 b |
| 'Pennington #5' (unpatented) | 24.0 ab | 155.1 b | 1.72 bc |
| 'Pennington #6' (unpatented) | 19.9 b | 142.1 b | 1.16 c |

[z]Diameter of the largest trunk at 10 cm above the soil surface.
[y]Distance from the soil surface to the apex of the tallest shoot.
[x]Canopy volume was calculated by multiplying the shoot height by the horizontal canopy area (area of an ellipse calculated from the north-south and east-west canopy diameter measurements).
[w]Means within each column followed by the same letter are not significantly different at $P \leqq 0.05$ according Student's T-test. N = 1 for 'September Sun', N = 8 for 'Blue River #6' and 'Pennington #5', N = 10 for 'Pennington #6'. Dunnett's test for comparing treatment groups against a control (Stevens, 1990) was used to confirm differences between 'September Sun' and the three half-sibling groups.

To facilitate the identification of the variety, the Macbeth-Munsell Disk Colorimeter was used to specifically identify colors of the important plant parts. The top side of the young leaf emerging from twigs is 5 GY 4/6. The lower side of the young leaf emerging from twigs is 5 GY 5/4. The top side of the mature leaf is 7.5 GY 2/4. The fall foliage is variegated, but the most predominant color is 7.5 Y 7/6. The Male inflorescence or flower cluster is 2.5 Y 7/6. The female inflorescence is 10 RP 4/12. The fully mature fruiting structure, or strobili, is 10 YR 2/1.

We claim:

1. A new and distinct variety of seaside alder plant named 'September Sun,' substantially as herein shown and described, characterized by fast growth, dense foliation, and symmetrically shaped individual plants that become mottled blends of orange, yellow and rich brown in autumnal conditions.

* * * * *